United States Patent [19]

Dennhoven et al.

[11] 4,210,811

[45] Jul. 1, 1980

[54] DRIVE FOR MOVEABLE SHIELD IN LUGGAGE SCREENING APPARATUS

[75] Inventors: Manfred Dennhoven, Wiesbaden; Claus Kunze, Taunusstein, both of Fed. Rep. of Germany

[73] Assignee: Heimann GmbH, Wiesbaden-Dotzheim, Fed. Rep. of Germany

[21] Appl. No.: 945,097

[22] Filed: Sep. 22, 1978

Related U.S. Application Data

[63] Continuation of Ser. No. 734,333, Oct. 20, 1976, abandoned.

[30] Foreign Application Priority Data

Nov. 3, 1975 [DE] Fed. Rep. of Germany ....... 2549211

[51] Int. Cl.$^2$ ............................................. G01K 23/00
[52] U.S. Cl. ................................ 250/358 R; 250/360; 318/135
[58] Field of Search ................... 250/358 R, 359, 360; 318/135

[56] References Cited

U.S. PATENT DOCUMENTS

| | | | |
|---|---|---|---|
| 3,135,880 | 6/1964 | Olson et al. | 318/135 |
| 3,678,278 | 7/1972 | Pell | 250/358 R |
| 3,852,600 | 12/1974 | Faulkner et al. | 250/360 |
| 3,891,907 | 6/1975 | Lenzkes et al. | 318/135 |
| 4,020,346 | 4/1977 | Dennis | 250/358 R |

*Primary Examiner*—Alfred E. Smith
*Assistant Examiner*—Janice A. Howell
*Attorney, Agent, or Firm*—Hill, Van Santen, Steadman, Chiara & Simpson

[57] ABSTRACT

An apparatus for inspecting or screening articles, such as closed luggage and parcels, having a moveable shield to enclose selectively a monitoring duct area in which the articles are placed for screening by X-ray or similar radiation. The shield moves in a fixed housing (which may in turn be mobile) on wheels. A linear drive motor has a stator fixed in the bottom of the housing. The shield carries a rail electromagnetically reactable directly with the stator. Proximity switches in the housing activated by a magnet on the shield control the travel of the shield. A switch located between the end of travel switches may be employed to vary the speed of the linear motor to provide quick, safe cycling of the apparatus.

5 Claims, 2 Drawing Figures

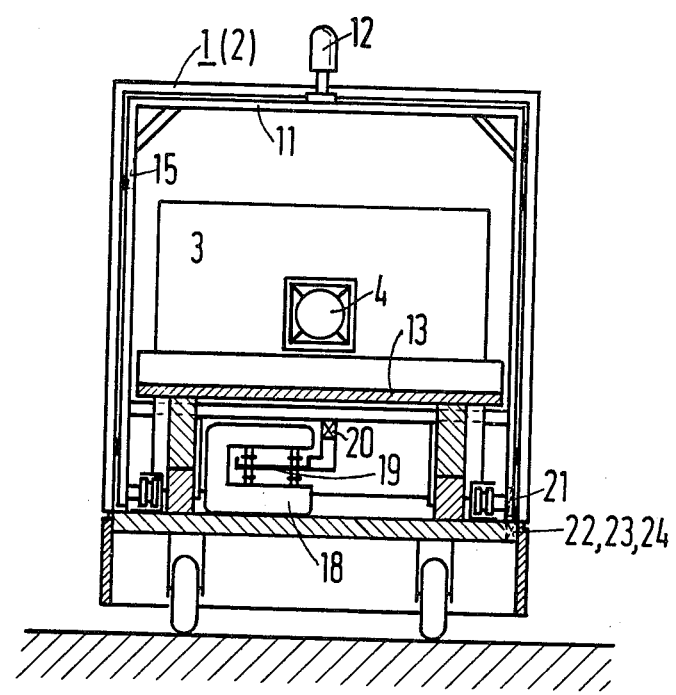

DRIVE FOR MOVEABLE SHIELD IN LUGGAGE SCREENING APPARATUS

This is a continuation of application Ser. No. 734,333, filed Oct. 20, 1976, now abandoned.

BACKGROUND OF THE INVENTION

1. Field of the Invention

The present invention relates to devices for inspecting sealed articles of luggage by passing X-ray radiation therethrough.

2. The Prior Art

Luggage inspection apparatus commonly employs a radiation source such as an X-ray generator which produces upon a fluorescent screen a shadow image which can be read directly or indirectly. The device has a lead-lined housing which protects the operators and environment against any escape of radiation. In one variety of inspection apparatus a monitoring duct extends parallel to the screen. A test object is placed within the duct and the duct is closed off by a moveable shield during irradiation of the article. The shield is moved with the assistance of a motor drive arrangement.

U.S. Pat. No. 3,678,278 discloses a device for luggage inspection wherein forward and backward movement of a shield is effected by a drive mechanism having a chain driven by a sprocket wheel on the output shaft of a conventional motor. A slip clutch is provided to prevent possible injury to persons reaching into the monitoring duct. Such drive system requires specially designed wearing parts in the transmission as well as parts requiring special maintenance. In any event these parts reduce the reliability of the installation. Variation in speed of the screen to provide a quick start up with slowing toward the end of the movement in both forward and reverse directions is difficult to obtain with such a drive.

Thus an object of the present invention is to provide a largely maintenance-free, easily controllable motor drive system for the moveable screen of a luggage inspection apparatus, the apparatus being completely protected from escape of X-rays. In accordance with the invention, a linear motor system is employed. As those skilled in the art will appreciate, a linear motor has only a single moving part, either an electromagnetic metal rail or a stator, one of which is linearly displaced by an electromagnetic reaction in the rail to a traveling magnetic field developed by the stator. A linear motor is particularly compact and is readily adjustable both for speed of displacement and for thrust force developed by the motor.

SUMMARY OF THE INVENTION

In a radiation-screening apparatus for sealed articles such as parcels and luggage, a moveable shield selectively encloses a monitoring duct placed between a radiation generator and a fluorescent shadow screen. Drive means for moving the shield with respect to a fixed, enclosing housing of the apparatus comprises an electromagnetically operable linear motor having a rail and a stator, one of the parts being attached directly to the shield and the other being fixed in the housing. Electric switches actuated by movement of the shield control the thrust and speed of the linear motor. The switches are conveniently provided as proximity switches actuated by a magnet. In one embodiment of the invention, the linear motor is set to produce a thrust force which is just insufficient to displace the moveable screen. The linear motor then acts as servo drive system to facilitate manual opening and closing of the screen of the monitoring duct. Its manual operation is simple and does not require any substantial work by an operator but avoids injury to persons and objects in the path of the shield. A handle on the moveable screen assists such manual, servo-assisted operation as well as operation of the shield in the event of electrical or control failure in the drive system.

THE DRAWINGS

FIG. 2 is a transverse, sectional view taken on line II—II of FIG. 1.

THE PREFERRED EMBODIMENTS

Figure 1:
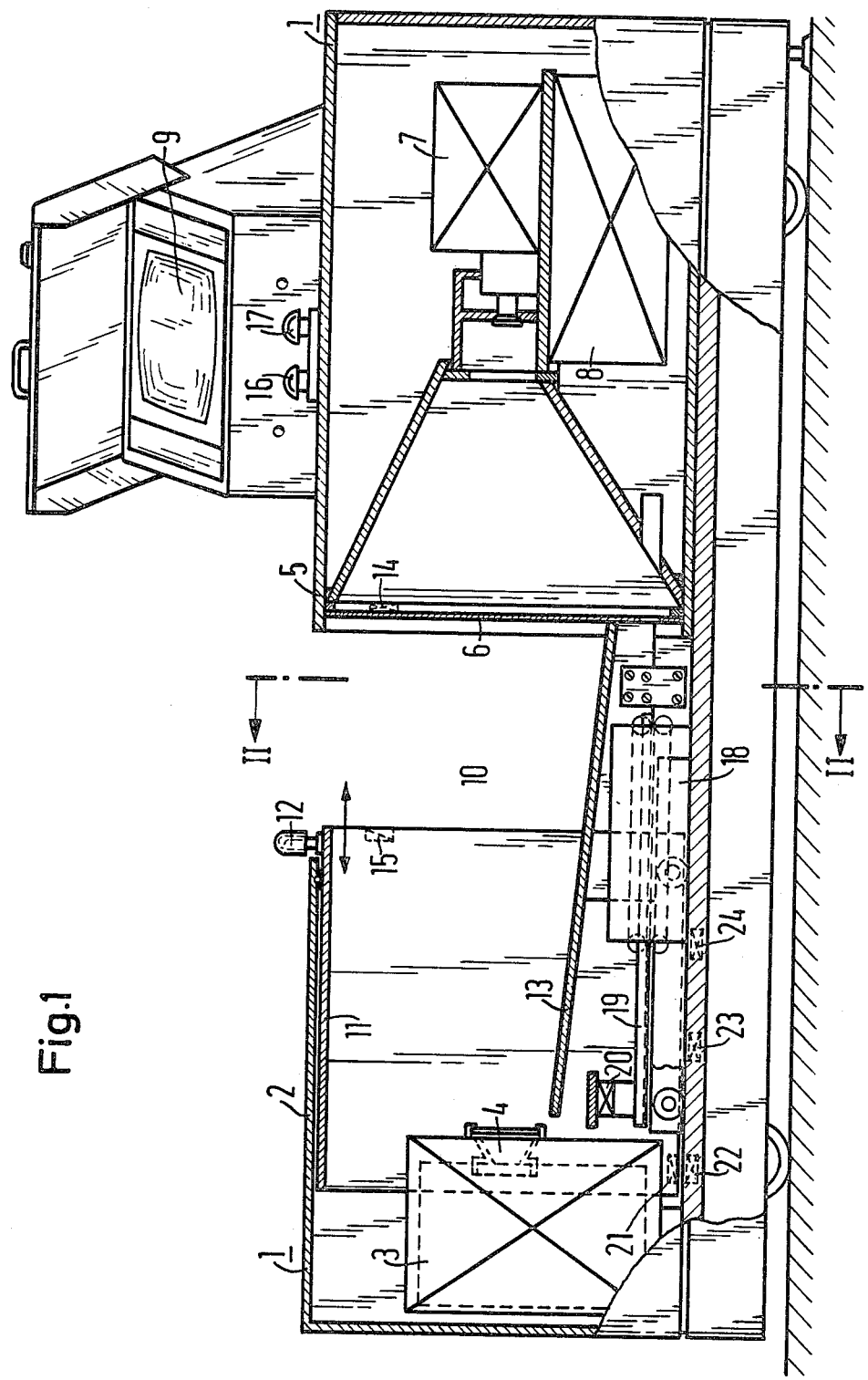
FIG. 1 is a longitudinal, sectional view, partially schematic, of the apparatus of the invention.

FIG. 1 discloses a luggage inspection installation such as is commonly found in airport terminals for screening against carrying of weapons onto airplanes. A fixed housing 1 encloses the apparatus and protects the environment against escape of X-radiation. A left-hand part 2 of the housing 1 encloses an X-ray generator 3 having a conical radiation exit aperture 4. A right-hand part 5 of the housing 1 carries a fluorescent screen 6 onto which a high-sensitivity television camera 7 is focussed for indirect viewing of shadow images created on the screen 6. An electronic control and signal storage unit 8 for coordinating initiation of X-radiation from the generator 3 and triggering of the camera 7. The electronic unit 8 preserves the shadow image upon a television monitor 9 for inspection by an operator of the apparatus. A monitoring duct 10 is formed between the parts 2 and 5 of the housing 1 for receiving items of luggage, parcels, and other articles for screening inspection.

A moveable, three-sided shield 11 is arranged to enclose the duct 10 selectively during execution of radiation screening. A platform 13 seals the bottom of the duct 10 against downwardly-scattered radiation. Closing of the shield 11 actuates a gas-filled switch 14 by a magnet 15 on a forward edge of the shield, permitting production of a starting pulse which triggers emission of X-radiation from the generator 3. The radiation penetrates through the article within the duct 10. A shadow picture of the article produced on the fluorescent screen 6 is picked up by the TV camera 7 and recorded for observation on the monitor 9. A handle 12 atop the shield 11 facilitates manipulation of the screen 11.

In accordance with the invention, beneath the platform 13 a linear motor means comprises a rail 19 and a stator 18 arranged in a horizontal position, i.e., parallel to the travel direction of shield 11, and is connected to a motor control means, which in turn is connected to an electrical power source (not shown). A rail 19 constructed of a conductive metal such as copper reacts magnetically with the stator 18 as does a rotor in a conventional motor. The rail 19 is driven through the stator 18 in a linear fashion. The rail 19 attaches through a coupling 20 directly to the moveable shield 11. The coupling 20 is of an elastic construction, to absorb any misalignment between the shield 11 and the rail 19. Guide wheels provided between the stator and the rail prevent contact therebetween and support the rail so that a very low force is required to move the rail relative to the stator.

The linear motor 18, 19 is activated by push buttons 16, 17 arranged on a control console adjacent the TV monitor 9. Preferably forward and backward movements are initiated by either of the buttons 16, 17, for safety purposes. Immediate reversal of the direction of motion can be made at any point in the travel of the shield 11.

For further, automatic control of shield movement, three gas-filled switches 22, 23, and 24 are set into the housing 1 adjacent the path of travel of a magnet 21 arranged as an activating device on the moveable shield 11. The end contacts 22, 24 switch drive coils of the linear motor 18 off at the respective terminal positions of the shield 11. The center switch 23 reduces the power and speed of movement of the linear motor and initiates a braking of the motor. This additional circuit permits an initially fast closing motion to the shield 11. The shield is slowed in mid-stroke for safety purposes, while a fast cycling speed is maintained. In any event the thrust force and speed of the linear motor 18, 19 can be adjusted extremely accurately by increased activation of the brake windings thereof.

In one special embodiment, the thrust force of the motor 18, 19 is adjusted to a value just below that required to move the shield 11. Then the motor electromagnetically operated linear motor means comprised of stator 18 and rail 19 acts as a servo drive system for manual operation of the shield 11, providing an especially safe operation. The operator need only overcome a portion of the friction and inertia of the shield 11 to effect closing or opening thereof.

It is also to be noted that use of the linear motor provides a very simple and reliable drive mechanism having only a single moving part i.e., the rail. No chain, hydraulic, or other system has such reliability and low maintenance requirements. Additionally, in the event of any electrical and the like failure in the system, the device of the present invention may be operated entirely by hand due to the lack of interference by the deactivated drive with movement of the shield (since there is substantially no mechanical or fluid coupling between the stator 18 and rail 19 of the electromagnetic motor means). An hydraulic control cannot be operated at all when deactivated, while a chain drive could be operated if at all only with great difficulty. Various additional alternate control devices may be added to the embodiment disclosed, as for instance to provide additional safety switches to prevent operation of the radiation generator if the shield does not completely close. Means for preventing opening of the shield about the monitoring duct may also be provided until radiation generation has ceased.

Although these and various other minor modifications may be suggested by those versed in the art, it should be understood that we wish to embody within the scope of the patent warranted hereon all such modifications as reasonably and properly come within the scope of our contribution to the art.

We claim as our invention:

1. In a radiation-screening apparatus for inspecting sealed articles such as parcels and luggage, including a moveable shield selectively enclosing a monitoring duct, and drive means for moving said shield with respect to a fixed housing of said apparatus, the improvement comprising wherein:
   said drive means comprises:
   an electromagnetically operable linear motor means having a rail and a stator, one of said rail and stator being attached to the shield and the other being fixed in the housing; and motor control means connected to said linear motor means and to an electrical power supply, said control means including three proximity switches and an activator, said switches and activator being mounted to be moveable relative to each other, two of said switches comprising limit end switches terminating electrical power to drive said linear motor at opposite ends of travel of said shield and the third proximity switch comprising a braking switch reducing electrical power to said linear motor between opposite ends of travel of said shield.

2. In a radiation-screening apparatus for inspecting sealed articles such as parcels and luggage, which includes a moveable radiation shield selectively enclosing a monitoring duct and drive means for moving said shield between two terminal positions relative to a fixed housing of said apparatus, the improvement comprising wherein:
   said drive means comprises;
   an electromagnetically operable linear motor means having an electrically conductive rail and a stator, one of said rail and stator being attached to said moveable shield and the other being attached to said fixed housing; and
   motor control means operationally connected to said linear motor means and to an electrical power source, said control means including a pair of electromagnetic proximity switches and an activating device, said proximity switches and activating device being mounted on said apparatus so as to be moveable relative to each other for at least terminating electical power to said motor means at said terminal positions of said shield.

3. In a radiation-screening apparatus as defined in claim 2 wherein said electrically conductive rail is attached to said moveable shield and said stator is attached to said fixed housing.

4. In a radiation-screening apparatus as defined in claim 3 wherein said electrically conductive rail is attached to said moveable shield via a flexible coupling member.

5. In a radiation-screening apparatus as defined in claim 2 wherein said control means includes at least a third proximity switch mounted on said apparatus so as to be moveable relative to said activating device, said third proximity switch decreasing electrical power to said motor means during shield movement between said terminal positions.

* * * * *